United States Patent
Russell (10) Patent No.: US 12,031,117 B2
(45) Date of Patent: Jul. 9, 2024

(54) PERFUSION BIOREACTOR SYSTEM AND PERFUSION CELL CULTURE METHOD

(71) Applicant: CORNING INCORPORATED, Corning, NY (US)

(72) Inventor: Ryann Loren Russell, Drexel Hill, PA (US)

(73) Assignee: CORNING INCORPORATED, Corning, NY (US)

( * ) Notice: Subject to any disclaimer, the term of this patent is extended or adjusted under 35 U.S.C. 154(b) by 1086 days.

(21) Appl. No.: 16/765,666

(22) PCT Filed: Nov. 20, 2018

(86) PCT No.: PCT/US2018/062073
§ 371 (c)(1),
(2) Date: May 20, 2020

(87) PCT Pub. No.: WO2019/104071
PCT Pub. Date: May 31, 2019

(65) Prior Publication Data
US 2020/0332242 A1    Oct. 22, 2020

Related U.S. Application Data

(60) Provisional application No. 62/589,669, filed on Nov. 22, 2017.

(51) Int. Cl.
*C12M 1/00* (2006.01)
*C12M 1/06* (2006.01)
(Continued)

(52) U.S. Cl.
CPC ............ *C12M 29/10* (2013.01); *C12M 21/08* (2013.01); *C12M 23/28* (2013.01); *C12M 27/02* (2013.01); *C12M 29/18* (2013.01); *C12M 37/00* (2013.01)

(58) Field of Classification Search
CPC ...... C12M 29/10; C12M 29/18; C12M 21/08; C12M 23/28; C12M 27/02; C12M 37/00;
(Continued)

(56) References Cited

U.S. PATENT DOCUMENTS 5,002,890 A  *  3/1991  Morrison ............... C12M 23/06
                                                          210/396
5,661,023 A       8/1997  Prior et al.
(Continued)

FOREIGN PATENT DOCUMENTS

CN    104762254 A    7/2015
CN    106620710 A    5/2017
(Continued)

OTHER PUBLICATIONS

International Search Report and Written Opinion of the International Searching Authority; PCT/US2018/062073; Mailed Feb. 11, 2019; 13 Pages; European Patent Office.
(Continued)

*Primary Examiner* — Michael L Hobbs
(74) *Attorney, Agent, or Firm* — Chandra J. Duncan (57) ABSTRACT

A perfusion bioreactor system that includes assemblies for separating cells from microcarriers and exchanging liquids in the perfusion bioreactor system is provided herein. The perfusion bioreactor system includes a vessel having a wall at least partially defining an interior compartment for receiving fluid, at least one port fluidly connected to at least one of a plurality of external sources and at least one outlet fluidly connected to a small pore membrane device.

7 Claims, 3 Drawing Sheets (51) Int. Cl.
*C12M 1/12* (2006.01)
*C12M 3/00* (2006.01)

(58) Field of Classification Search
CPC ...... C12M 25/14; C12M 25/16; C12M 33/14; C12M 47/02
See application file for complete search history.

(56) References Cited

U.S. PATENT DOCUMENTS

| | | | |
|---|---|---|---|
| 6,190,913 | B1 | 2/2001 | Singh |
| 7,481,572 | B2 | 1/2009 | Terentiev |
| 9,217,129 | B2 | 12/2015 | Moretti et al. |
| 2002/0022270 | A1* | 2/2002 | Emerson ............ C07K 14/5403 435/372 |
| 2008/0280300 | A1 | 11/2008 | Choo |
| 2009/0042253 | A1 | 2/2009 | Hiller |
| 2015/0247117 | A1* | 9/2015 | Jia ............................ D21C 5/00 435/252.4 |
| 2016/0145567 | A1 | 5/2016 | Henry et al. |
| 2021/0269477 | A1* | 9/2021 | Konstantinov .......... C07K 1/34 |
| 2022/0186178 | A1 | 6/2022 | Henry et al. |

FOREIGN PATENT DOCUMENTS

| | | |
|---|---|---|
| EP | 0338716 A2 | 10/1989 |
| JP | 10-500286 A | 1/1998 |
| JP | 2009-517072 A | 4/2009 |
| JP | 2010-029109 A | 2/2010 |
| JP | 2016-523086 A | 8/2016 |
| JP | 2016-530893 A | 10/2016 |
| WO | 2015/039115 A1 | 3/2015 |
| WO | 2016/200888 A1 | 12/2016 |
| WO | 2017/112455 A2 | 6/2017 |

OTHER PUBLICATIONS

Spectrum Laboratories< Inc., "Conversion of Bioreactors to Continuous Perfusion Using Hollow Fiber Cell Separators", Jan. 1, 1989, XP55155533, Retrieved from the Internet: URL:http://www.spectrumlabs.com/lit/CPAG.pdf.
"Conversion of Bioreactors to Continuous Perfusion Using Hollow Fiber Cell Separators", 1989, Retrieved from the Internet <URL:http://www.spectrumlabs.com/lit/CPAG.pdf, 30 pages.
Japanese Patent Application No. 2020-528304, Office Action dated Sep. 12, 2022, 6 pages (English Translation onlyj), Japanese Patent Office.
Chinese Patent Application No. 201880075903.2, Office Action, dated Feb. 10, 2023, 5 pages Chinese Patent Office.

* cited by examiner

PERFUSION BIOREACTOR SYSTEM AND PERFUSION CELL CULTURE METHOD

CROSS REFERENCE TO RELATED APPLICATIONS

This is a national stage application under 35 U.S.C. § 371 of International Application No. PCT/US2018/062073, filed on Nov. 20, 2018, which claims the benefit of priority of U.S. Provisional Application Ser. No. 62/589,669 filed on Nov. 22, 2017, the contents of which are relied upon and incorporated herein by reference in their entirety as fully set forth below.

FIELD

The present disclosure generally relates to perfusion bioreactor systems and, more particularly, to perfusion bioreactor systems including assemblies for separating cells from microcarriers and exchanging liquids in the perfusion bioreactor systems.

BACKGROUND

Microcarrier cell culturing is typically carried out in a bioreactor. During culturing, the cells grow on the surface of the microcarriers. Once the cell culturing process is completed, the cultured cells are detached from the microcarriers and the cultured solution containing the cells is then separated from the microcarriers for use or further processing.

One conventional technique for separating microcarriers from the cultured solution that includes the detached cells includes passing the solution through a rigid mesh screen in a container. The screen allows the cultured fluid to pass through but prevents the microcarriers from doing so. However, as the microcarriers build up on the screen, they begin to clog the screen and prevent the fluid from passing therethrough. The clogged microcarriers also can trap cells and prevent the cells from passing through the mesh screen. Once the screen is clogged, the process stops until the screen is unclogged. These process steps can be expensive and time consuming and are also believed to contribute to reduced cell yield in microcarrier cell culture. Furthermore, because the mesh screen is a separate system component, the cultured solution must be transferred from the vessel in which the cell culture process is being performed to be passed through the mesh screen. As a result of this transfer, such mesh screens may increase risks of contaminating the cells or the cell culture solution.

Several other techniques for separating microcarriers from the cultured solution that includes the detached cells include, for example, differential gradient centrifugation, acoustic resonance, tangential flow filtration, spin filters and sedimentation using conical or inclined plates. Most of these techniques require expensive capital equipment or are complex to operate. One commercially available device that provides a technique for separating microcarriers from the cultured solution that includes the detached cells that is relatively less complex is the HyQ Harvestainer.

The HyQ Harvestainer is able to accommodate hundreds of liters of medium and depends upon a pump to pass cells, microcarriers and culture medium through the device. More specifically, the HyQ Harvestainer has a mesh bag inside a larger structured liquid impermeable bag that has an outlet for the filtered medium. The microcarriers are repeatedly washed and the cells are enzymatically separated from the microcarriers in an external bioreactor before the solution of cells, microcarriers, and medium are perfused into and through the HyQ Harvestainer. The microcarriers are retained in the inner mesh bag of the HyQ Harvestainer, and the cells and medium pass through the inner mesh bag and then out of the structured outer bag into a cell collection container. As can be appreciated, the steps required make use of the HyQ Harvestainer cumbersome.

SUMMARY

According to embodiments of the present disclosure, a perfusion bioreactor system is provided herein. The perfusion bioreactor system includes a vessel having a wall at least partially defining an interior compartment for receiving fluid, at least one port fluidly connected to at least one of a plurality of external sources and at least one outlet fluidly connected to a small pore membrane device.

According to embodiments of the present disclosure, a perfusion cell culture method is provided. The method includes adding cells and cell growth medium to a vessel of a bioreactor system and adding dissolvable microcarriers to the vessel. The method further includes removing spent medium by flowing medium from the vessel to at least one membrane device fluidly connected to the vessel and adding fresh medium to the vessel to replace the removed spent medium. Additionally, the method includes dissolving the dissolvable microcarriers, and removing spent medium with dissolved microcarrier material from the vessel by flowing medium from the vessel to the at least one membrane device fluidly connected to the vessel.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

The disclosure will be understood more clearly from the following description and from the accompanying figures, given purely by way of non-limiting example, in which.

DETAILED DESCRIPTION

Reference will now be made in detail to the present embodiment(s), an example(s) of which is/are illustrated in the accompanying drawings. Whenever possible, the same reference numerals will be used throughout the drawings to refer to the same or like parts.

The singular forms "a," "an" and "the" include plural referents unless the context clearly dictates otherwise. The endpoints of all ranges reciting the same characteristic are independently combinable and inclusive of the recited endpoint. All references are incorporated herein by reference.

As used herein, "have," "having," "include," "including," "comprise," "comprising" or the like are used in their open ended sense, and generally mean "including, but not limited to."

All scientific and technical terms used herein have meanings commonly used in the art unless otherwise specified. The definitions provided herein are to facilitate understanding of certain terms used frequently herein and are not meant to limit the scope of the present disclosure.

The present disclosure is described below, at first generally, then in detail on the basis of several exemplary embodiments. The features shown in combination with one another in the individual exemplary embodiments do not all have to be realized. In particular, individual features may also be omitted or combined in some other way with other features shown of the same exemplary embodiment or else of other exemplary embodiments.

Embodiments of the present disclosure relate to perfusion bioreactor systems and perfusion cell culture methods. Systems and methods as described herein utilize dissolvable microcarriers and at least one perfusion membrane devices to facilitate performance of several cell culture processes which are conventionally performed using separate systems or hardware within a single vessel of a bioreactor system. As such, systems and methods as described herein effectively reduce the costs associated with growing cells, separating cells from growth surfaces, and harvesting cells or other cell products from the systems. Thus, by facilitating performance of the cell culture and separation processes within a single vessel of a bioreactor system, embodiments of the present disclosure also reduce contamination risks and cell yield losses associated with removing cells from an initial system or vessel and transferring cells to a subsequent system or vessel. Examples of reduced contamination risks include potential exposure of the cells or cell products with contaminants such as, for example, extractables and leachables from the materials of the various systems or vessels and/or particulates which may originate from the materials of the various systems or vessels, or which may originate from the environment during transfer of the cells or cell products from one system or vessel to another system or vessel. Exposure to such contaminants may lead to contamination of costly downstream products which may ultimately need to be discarded as a result of the contamination.

Embodiments of the present disclosure benefit from certain advantages in cell culture applications which are provided by dissolvable microcarriers. For cell culture it is conventional to grow cells on a cell adhering surface since most mammalian cells and certain other cells are anchorage-dependent to be able to grow. In contrast to cell culture on flat surfaces where adherent cells can reach high confluence and thus limit cell expansion via cell-to-cell contact inhibition, microcarriers having a high ratio of surface area/volume present an attractive platform for efficient cell culture scale-up or expansion where either harvested cells, cell-based products, or conditioned medium can be the desired product. While microcarriers formed from plastic materials have previously been used for cell culture, dissolvable microcarriers, or microcarriers which can be controllably dissolved to separate cells from the surface of the microcarrier, are providing certain advantages in cell culture applications.

As will become clearer in the discussions below, dissolvable microcarriers as disclosed herein are described as being dissolvable and insoluble. As used herein, the term "insoluble" is used to refer to a material or combination of materials that is not soluble, and that remains solid, under conventional cell culture conditions which include, for example, cell culture medium. Also as used herein, the term "dissolvable" is used to refer to a material or combination of materials which enters solution when exposed to a condition which causes the material or combination of materials to enter solution. According to a non-limiting example, the material or combination of materials may be digested when exposed to an appropriate concentration of an enzyme that digests or breakdowns the material or combination of materials. According to alternative non-limiting examples, the material or combination of materials may enter solution when exposed to a range of temperatures or a range of pH values.

Dissolvable microcarriers of embodiments of the present disclosure may be, for example, those disclosed in U.S. Patent Application Publication No. 2016/0145567 A1 and PCT Application Publication No. 2016/200888 A1, the contents of which are incorporated herein by reference in their entirety.

Dissolvable microcarriers as described herein may include at least one ionotropically cross-linked polysaccharide. The polysaccharide may be, for example, pectic acid, also known as polygalacturonic acid (PGA), or a salt thereof, or partly esterified pectic acid known as pectinic acid, or a salt thereof. The dissolvable microcarriers may be crosslinked to increase their mechanical strength and to prevent the dissolving of the microcarriers when placed in contact with cell culture medium. Crosslinking may be performed by ionotropic gelation wherein ionotropic gelation is based on the ability of polyelectrolytes to crosslink in the presence of multivalent counter ions to form crosslinked microcarriers. Without wishing to be bound by any particular theory, it is believed that ionotropic gelation of the polysaccharide of the dissolvable microcarriers is the result of strong interactions between divalent cations and the polysaccharide.

According to embodiments of the present disclosure, dissolvable microcarriers as described herein may further include an adhesion polymer coating. The adhesion polymer may include peptides. Exemplary peptides may include, but are not limited to BSP, vitronectin, fibronectin, laminin, Type I and IV collagen, denatured collagen (gelatin), and like peptides, and mixtures thereof. Additionally, the peptides may be those having an RGD sequence. The coating may be, for example, Synthemax® II-SC (commercially available from Corning, Incorporated, Corning, NY).

Dissolvable microcarriers as described herein may be dissolved when exposed to a condition which causes the dissolvable microcarrier material to enter solution. Such a condition may be, for example, a range of temperatures, a range of pH values, or a digestion agent. As one example, the dissolvable microcarrier may be digested when exposed to a digestion agent which includes an appropriate enzyme that digests or breakdowns the microcarrier. Non-proteolytic enzymes suitable for digesting the microcarriers, harvesting cells, or both, include pectinolytic enzymes or pectinases, which are a heterogeneous group of related enzymes that hydrolyze the pectic substances. Pectinases (polygalacturonase) are enzymes that break down complex pectin molecules to shorter molecules of galacturonic acid. Commercially available sources of pectinases are generally multi-enzymatic, such as Pectinex™ ULTRA SP-L (commercially available from Novozyme North American, Inc., Franklinton, NC), a pectolytic enzyme preparation produced from a selected strain of *Aspergillus aculeatus*. Pectinex™ ULTRA SP-L contains mainly polygalacturonase, (EC 3.2.1.15) pectintranseliminase (EC 4.2.2.2) and pectinesterase (EC: 3.1.1.11). The EC designation is the Enzyme Commission classification scheme for enzymes based on the chemical reactions the enzymes catalyze.

According to embodiments of the present disclosure, the digestion agent may also include a chelating agent. Exemplary chelating agents include, but are not limited to, ethylenediaminetetraacetic acid (EDTA), cyclohexanediaminetetraacetic (CDTA), ethylene glycol tetraacetic acid (EGTA), citric acid and tartaric acid.

Figure 1:
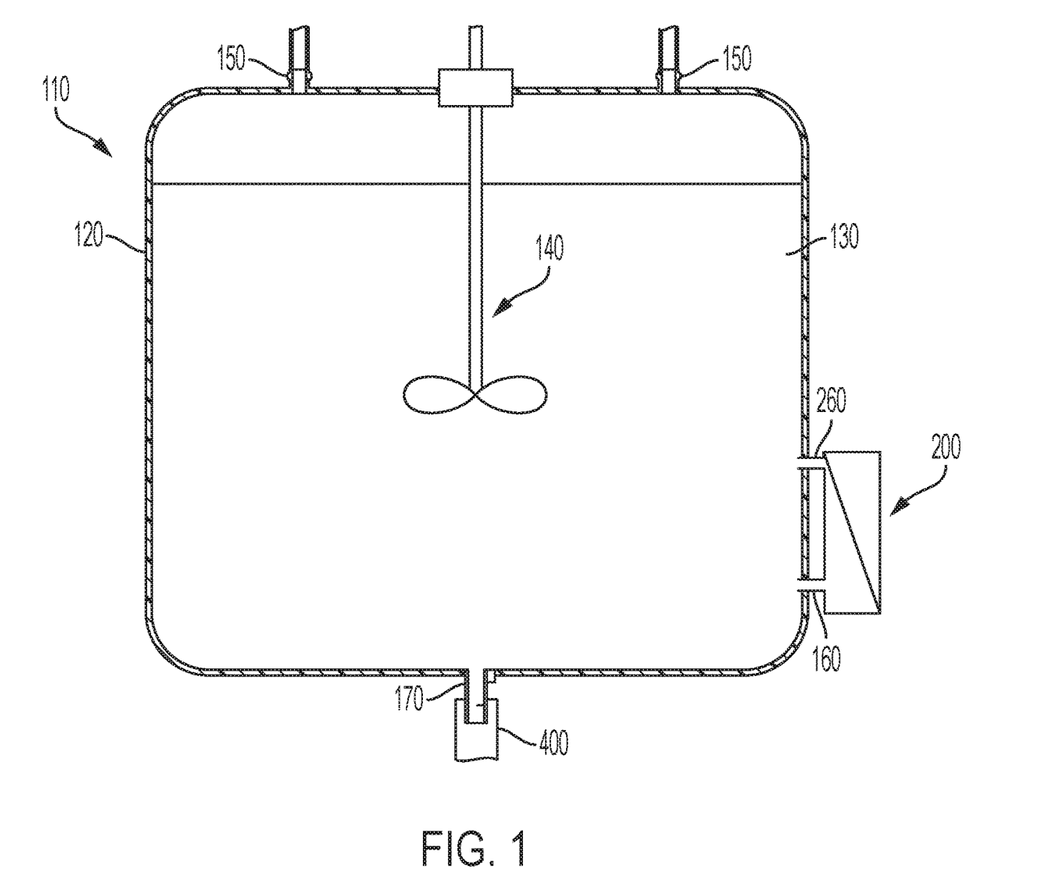
FIG. 1 schematically illustrates a perfusion bioreactor system in accordance with embodiments of the present disclosure.

FIG. 1 illustrates a perfusion bioreactor system in accordance with embodiments of the present disclosure. The bioreactor system 100 includes a vessel 110 having a wall 120 at least partially defining an interior compartment 130 for receiving fluid. The vessel 110 may be a flexible vessel formed from materials conventionally associated with disposable products for bioprocess applications. The vessel 110 may be formed from a film or laminate that includes at least one plastic material from the following group: polyethylene (PE), polypropylene (PP), polyvinyl chloride (PVC), polyethylene terephtalate (PET), polystyrene (PS), polycarbonate (PC), polymethylpentene (PMP), polyetheretherketone (PEEK) polytetrafluoroethylene (PTFE), polyfluoroalkoxy (PFA), polychlorotrifluoroethylene (PCTFE), ethylene vinyl acetate (EVA), and derivatives thereof. Alternatively, the vessel 110 may be a rigid vessel formed from relatively rigid plastic materials such as, but not limited to, high density polypropylene (HDPE), ultrahigh molecular weight (UHMW) polyethylene, polypropylene, EVA, LDPE and LLDPE. Optionally, the vessel 110 may be formed from glass, metal or another rigid material.

As used herein, the term "fluid" refers to any substance capable of flowing, such as liquids, liquid suspensions, gases, gaseous suspensions, or the like, without limitation. The term "fluid and/or other components" is used throughout the present disclosure to refer to fluid which may include cell culture medium having nutrients for cell growth, cells, byproducts of the cell culture process, and any other biological materials or components that may conventionally be added or formed in a bioprocess system. Vessels described herein may include one or more cells or reagents. The vessels may also include buffers. Additionally, the vessels may include cell culture medium. Cell culture medium may be for example, but is not limited to, sugars, salts, amino acids, serum (e.g., fetal bovine serum), antibiotics, growth factors, differentiation factors, colorant, or other desired factors. Common culture medium that may be provided in the vessels includes Dulbecco's Modified Eagle Medium (DMEM), Ham's F12 Nutrient Mixture, Minimum Essential Media (MEM), RPMI Medium, and the like. Any type of cultured cell may be included in the vessels including, but not limited to, immortalized cells, primary culture cells, cancer cells, stem cells (e.g., embryonic or induced pluripotent), etc. The cells may be mammalian cells, avian cells, piscine cells, etc. The cells may be of any tissue type including, but not limited to, kidney, fibroblast, breast, skin, brain, ovary, lung, bone, nerve, muscle, cardiac, colorectal, pancreas, immune (e.g., B cell), blood, etc. The cells may be in any cultured form in the vessels including disperse (e.g., freshly seeded), confluent, 2-dimensional, 3-dimensional, spheroid, etc. In some embodiments, cells are present without medium (e.g., freeze-dried, in preservative, frozen, etc.). As will be described in further detail below, vessels described herein may also include dissolvable microcarriers and/or dissolvable microcarrier material.

It should be understood that the dimensions of the vessel 110 including both relative and absolute dimensions can be varied. For example, the vessel 110 may be configured to hold a volume of fluid and/or other components of between about 1.0 mL and about 2,000 L. For example, the vessel 110 may be configured to hold a volume of fluid and/or other components of or about 100 mL, or about or about 250 mL, or about 500 mL, or about 1.0 L, or 5.0 L, or about 10 L, or about 50 L, or about 100 L, or about 250 L or even about 500 L, 1,000 L, 1,500 L, and 2,000 L, as well as all volumes therebetween.

Figure 2:
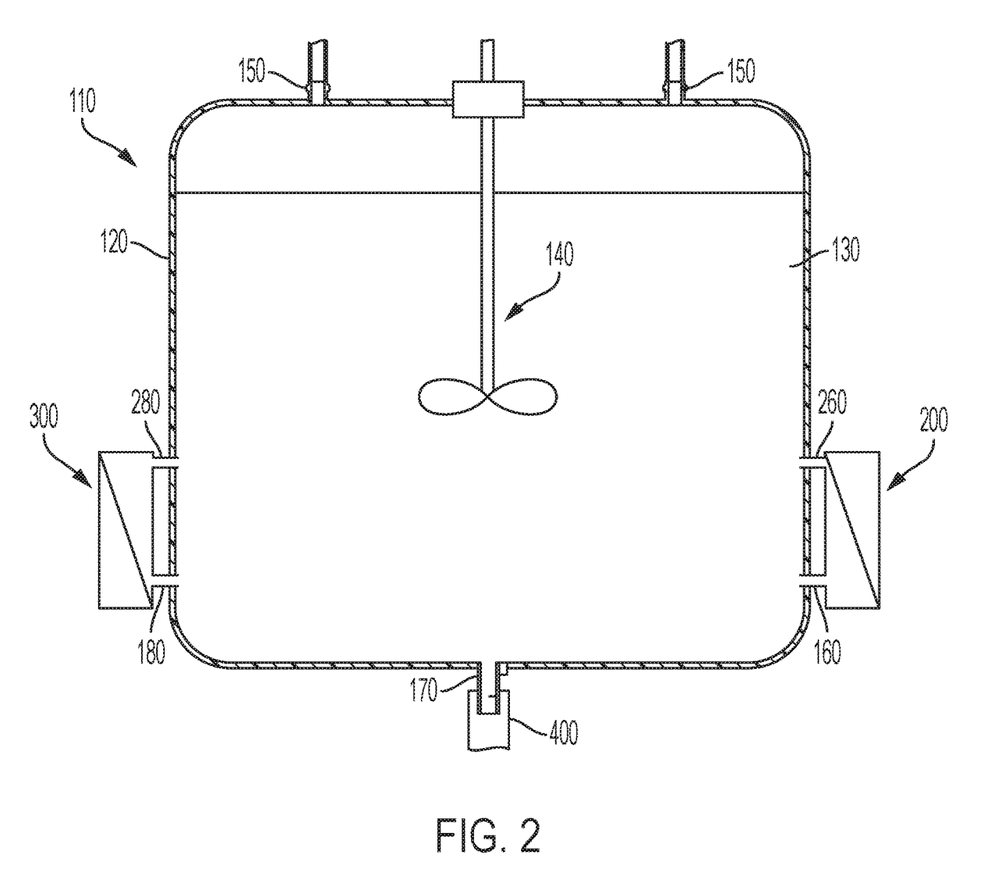
FIG. 2 schematically illustrates a perfusion bioreactor system in accordance with embodiments of the present disclosure.

As further shown in FIGS. 1-2, the vessel 110 may include an agitator 140 in the interior compartment of the vessel 110. The agitator 140 may include a shaft extending from the top of the vessel 110, the shaft having at least one impeller along the length of the shaft and being coupled to an overhead motor configured to rotate the at least one impeller within the interior compartment 130 of the vessel 110. Alternatively, the agitator 140 may include a shaft extending from the top of the vessel 110 and having a paddle at the end of the shaft. The shaft is coupled to an overhead motor which is configured to rotate the paddle through a substantially circular path at a nonzero angle relative to a central vertical axis of the vessel 110. An example of such a paddle-based agitator is shown in U.S. Pat. No. 9,168,497 B2. As another alternative, the agitator 140 may include a shaft extending from the top of the vessel 110 and having four paddle blades extending from, and contiguous with, the shaft with each of the paddle blades being disposed 90 degrees relative to each other. The four paddle blade agitator further includes a receptacle configured to house a magnetic stir bar which allows for the four paddle blade agitator to be rotated through magnetic induction. An example of such a four paddle blade agitator is shown in U.S. Pat. No. 8,057,092 B2. As yet another alternative, the agitator 140 may include a rotatable impeller disposed in the bottom of the interior compartment 130. The rotatable impeller is at least partially magnetic or ferromagnetic and may be magnetically coupled to an external motive device which includes a rotating drive magnet structure for forming a magnetic coupling with the fluid-agitating element, an electromagnetic structure for rotating and levitating the fluid-agitating element, or a superconducting element for both levitating and rotating the fluid-agitating element. An example of such a rotatable impeller is shown in U.S. Pat. No. 7,481,572 B2.

The agitator as described herein is an optional feature of the vessel 110 of the bioreactor system 100 and it should be understood that agitation may be performed in the vessel 110 of bioreactor system 100 in accordance with embodiments of the present disclosure without an agitator in the interior compartment 130 of the vessel 110. An example of a bioreactor system which does not include an agitator is an oscillating bioreactor system wherein the vessel includes a closed-loop chamber and the system includes an oscillating mechanism configured to move the closed-loop chamber bidirectionally along an axis horizontal to an axis normal to the closed-loop chamber to force convection of cells and fluid in the closed-loop chamber. An example of such an oscillating bioreactor system is shown in U.S. Pat. No. 9,217,129 B2. Another example of a bioreactor system which does not include an agitator is a wave bioreactor system wherein the vessel includes a pillow-shaped vessel which is placed on a rocking platform that moves it back and forth through a preset angle and at a preset rocking rate. The rocking motion induces waves in the culture media which promote agitation and oxygen transfer within the vessel. Such wave bioreactor systems are well known to a person of ordinary skill in the art, but are generally described, for example, in U.S. Pat. No. 6,190,913 B1.

The vessel 110 is hermetically sealed and may have one or more openings for introducing or recovering fluid and/or other components. Where the vessel 110 includes one or more openings, the one or more openings may include seals that in a first configuration expose the one or more openings to aseptic fluid communication between an external container and the interior compartment 130 of the vessel 110 through the opening. In a second configuration, the seals close the one or more openings and prevent or reduce fluid communication between the outside of the vessel 110 and the interior compartment 130 of the vessel 110 through the opening. The seals may take any desired form, including, but not limited to, a clamp, tape, a cap, a tube portion having a welded end, a zipper, a slide zipper, interlocking or coupling structures, aseptic connectors and the like.

As one example, FIGS. 1-2 show a vessel 110 in accordance with embodiments of the present disclosure having at least one port 150. The at least one port 150 may be disposed at the top of the vessel 110 or in a sidewall of the vessel 110. The at least one port 150 may be attached to at least one external source of fluid and/or other components. The external source may be, for example, a flexible or rigid vessel and may be connected and disconnected from the vessel 110 through any type of connection including, but not limited to, tube-welded connectors, aseptic connectors or other types of connectors. Optionally, the vessel 110 may include a plurality of ports which are each connected to one of a plurality of external sources. Alternatively, a plurality of external sources may be fluidly connected to a common tubing manifold which is itself in fluid communication with tubing attached to the at least one port 150. As yet another alternative, an aseptic connector may be disposed at, or in fluid communication with, the at least one port 150. Such an aseptic connector may allow for the disconnection of a first external source from the connector and subsequent connection of a subsequent external source to the connector while maintaining aseptic conditions within the bioreactor system 100. The external source may include one of cell culture medium, dissolvable microcarriers, cells, digestion agent, harvest formulation and final formulation.

FIG. 1 further illustrates a vessel 110 having a plurality of outlets 160, 170. As shown in FIG. 1, outlet 160 may be fluidly connected to a small pore membrane device 200, and outlet 170 may be fluidly connected to a cell harvest line 400. FIG. 2 illustrates an alternative vessel 110 further including outlet 180 fluidly connected to a large pore membrane device 300. The small pore membrane device 200 and the large pore membrane device 300 may include, for example, membranes that allow certain substances to pass through, while retaining others. Generally, substances that are small enough to pass through the membrane of the respective membrane device 200, 300 may be those which are regarded as waste and are discarded in a waste container disposed external to the vessel 110. However, it should be appreciated that certain cellular products, such as, but not limited to, antibodies or viruses, that are small enough to pass through the membrane of the respective membrane device 200, 300 may be regarded as a product to be collected in a container disposed external to the vessel 110 for downstream processing or use. As shown in the FIGS. 1-2, the small pore membrane device 200 may include an external recirculation loop that is run parallel to the vessel 110, and the large pore membrane device 300 may include an external recirculation loop that is run parallel to the vessel 110 and that is separate from a recirculation loop having the small pore membrane device 200. Substances that are too large to pass through the membrane of the respective membrane device 200, 300 may be retained in the vessel 110. Where the membrane devices 200, 300 include external recirculation loops, the substances that are too large to pass through the membrane of the respective membrane device 200, 300 may be returned to the vessel 110 through an inlet of the recirculation loop (i.e. inlet 260 from the small membrane device 200 and inlet 280 from the large membrane device 300). Alternatively, the substances that are too large to pass through the membrane of the respective membrane device 200, 300 may be returned to the vessel 110 in a reverse direction through the respective outlet 160, 180 of the vessel 110. It should be appreciated that substances passing through a membrane or substances not passing through a membrane generally describe the filtering capability of the membrane after flowing fluid and/or other components across the surface of the membrane a plurality of times. As such, as a result of several factors, on any single step of flowing fluid and/or other components over the surface of the membrane, substances small enough to pass through the membrane may not pass through the membrane and may instead be returned to the interior compartment 130 of the vessel 110. However, as the number of steps of flowing fluid and/or other components over the surface of the membrane increase, the likelihood that substances small enough to pass through the membrane will in fact pass through the membrane increases.

The membrane devices 200, 300 may be, for example, hollow fiber filters, tangential flow filtration devices, etc. Generally, the large pore membrane device 300 may include a membrane having an average pore size of between about 1 μm and about 100 μm and the small pore membrane device 200 may include a membrane having an average pore size of between about 0.1 μm and about 1 μm.

The average pore size of the large pore membrane device 300 is large enough to allow for the passage of spent medium with cellular waste products (e.g., recombinant protein, antibody, virus particles, DNA, RNA, sugars, lipids, biodiesel, inorganic particles, butanol, metaboloic byproducts) through the membrane, but small enough to prevent the passage of dissolvable microcarriers through the membrane and to retain the dissolvable microcarriers in vessel 110. Generally, fluid and/or other components may be directed out of outlet 180 to large pore membrane device 300 during the process of expanding cells on the surface of the dissolvable microcarriers.

The average pore size of the small pore membrane device 200 is large enough to allow for the passage of spent medium with cellular waste products through the membrane, but small enough to prevent the passage of cells through the membrane and to retain cells in vessel 110. The average pore size of the small pore membrane device 200 can be tailored for the size of the cells so that cell retention is optimum. Generally, fluid and/or other components may be directed out of outlet 160 to small pore membrane device 200 after the dissolvable microcarriers have been dissolved. Additionally, fluid and/or other components may generally be directed out of outlet 170 to the cell harvest line 400 following completion of cell expansion in the process of collecting a cell product from the bioreactor system 100.

FIGS. 1-2 illustrates a vessel 110 having three outlets. However, it should be appreciated that vessels 110 according to embodiments of the present disclosure are not so limited and may include any number of outlets so long as vessel 110 is fluidly connected to a small pore membrane device 200 and optionally a large pore membrane device 300. For example, vessel 110 may include one outlet fluidly connected to a tube which extends from the outlet to a region where the tube separates into at least two channels with one of the at least two channels being fluidly connected to a small pore membrane device 200 and another of the at least two channels being fluidly connected to a cell harvest line 400. The tube further includes a valve or a plurality valves which direct the flow of fluid and/or other components to one of the at least two channels and restrict the flow of fluid and/or other components to the other of the at least two channels.

Figure 3:
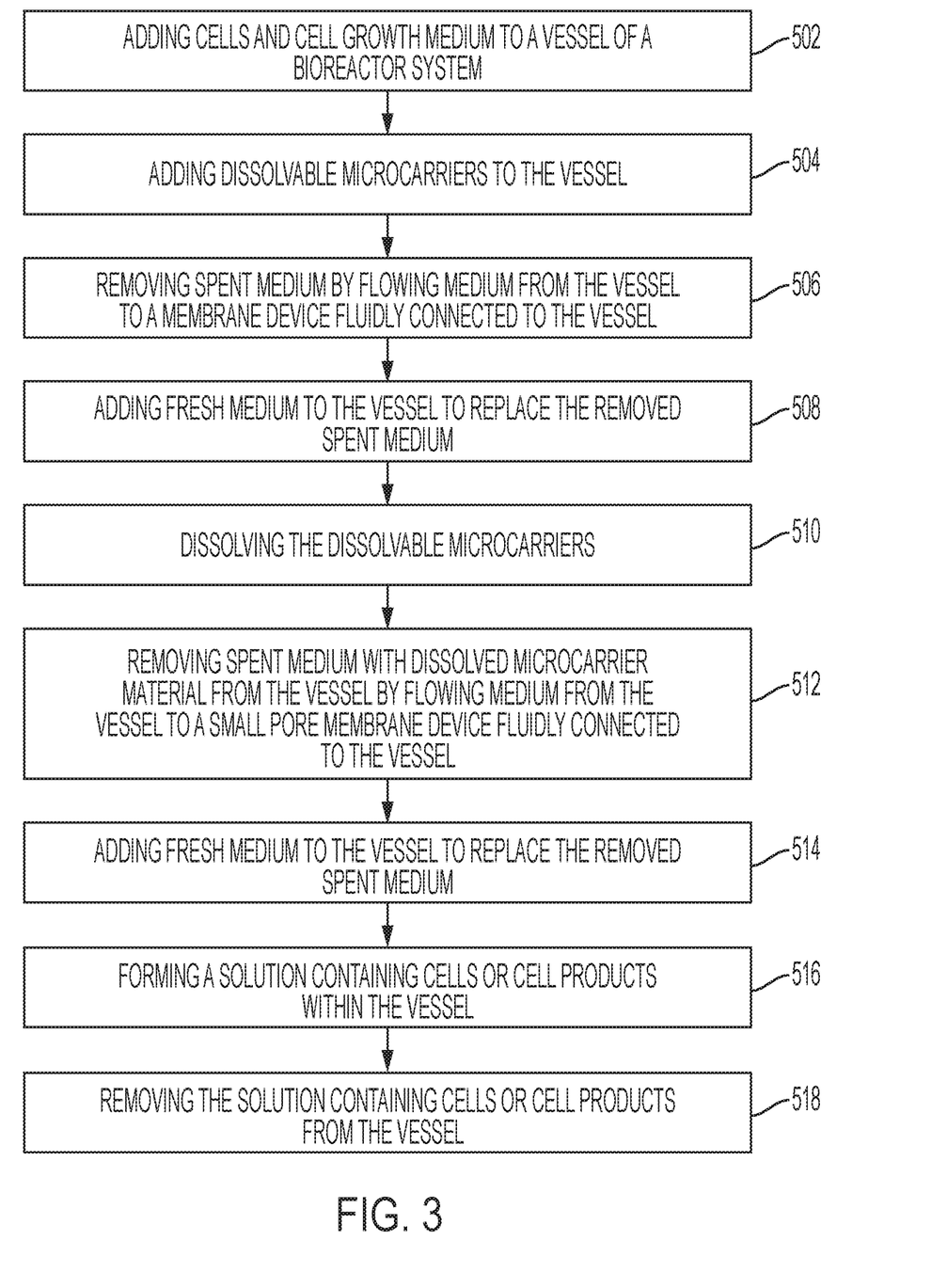
FIG. 3 illustrates a perfusion cell culture method in accordance with embodiments of the present disclosure.

Embodiments of the present disclosure further relate to a perfusion cell culture method. FIG. 3 illustrates an exemplary perfusion cell culture method according to embodiments of the present disclosure. Such perfusion cell culture method may be performed with perfusion bioreactor system 100 as described herein and as illustrated in FIGS. 1-2. As used herein, the term "perfusion" refers to culturing cells in which additional fresh medium or concentrated nutrient solution is provided, either continuously over some period of time or intermittently over some period of time, to the culture, and simultaneously spent medium is removed. The fresh medium typically provides nutritional supplements for the cells that have been depleted during the culturing process. Perfusion also allows for removal of cellular waste products and harvest byproducts, such as dissolved microcarrier material, from the bioreactor.

The perfusion cell culture method 500 as described herein may include adding 502 cells and cell growth medium to a vessel 110 of a bioreactor system 100. The perfusion cell culture method 500 as described herein may further include adding 504 dissolvable microcarriers to the vessel 110 of a bioreactor system 100. Any amount of dissolvable microcarriers may be added to the vessel 110 so long as enough dissolvable microcarriers are added to facilitate substantial confluence in the bioreactor system. As used herein, the terms "confluent" and "confluence" are used to refer to conditions when cells have formed a coherent monocellular layer on the surface of a cell culture substrate (i.e. the surface of a dissolvable microcarrier), so that virtually all the available surface is used. For example, "confluent" has been defined as the situation where all cells are in contact all around their periphery with other cells and no available substrate is left uncovered. For purposes of the present disclosure, the term "substantially confluent" is used to refer to conditions when cells are in general contact with the surface of the dissolvable microcarriers, even though interstices may remain, such that greater than about 70%, or greater than about 80%, or even greater than about 90%, of the available surface is used. The term "available surface" is used to mean sufficient surface area to accommodate a cell. Thus, small interstices between adjacent cells that cannot accommodate an additional cell do not constitute "available surface".

After cells, medium, and dissolvable microcarriers are added to the bioreactor system 100, growth of the cells within the vessel 110 occurs and continues until the cells occupy the dissolvable microcarrier surfaces until the cells are substantially confluent on the dissolvable microcarriers, or until the cells exceed the capacity of the medium to support further growth. Exceeding the capacity of the medium is the result of the cells consuming nutrients in the medium and produce waste products which can have direct negative effects on cell growth, cell health, and/or cell function.

As will become clear from the discussions of the perfusion cell culture method 500 below, growth and proliferation of the cells within the vessel 110 may continue by removing medium containing waste products and adding fresh medium to replace the removed medium. Generally, the perfusion cell culture method 500 can be performed with no significant change in the medium volume within the vessel 110. Alternatively, the perfusion cell culture method 500 can be performed such that the medium volume within the vessel 110 is increased at predetermined times during performance of the method.

According to embodiments of the present disclosure, the perfusion cell culture method 500 as described herein may further include removing 506 spent medium from the vessel 110 by flowing medium from the vessel 110 of the bioreactor system 100 to a membrane device 200, 300. Optionally, flowing medium from the vessel 110 of the bioreactor system 100 to a membrane device 200, 300 may include pumping the medium from the vessel 110 to an external recirculation loop that is fluidly connected to the vessel 110 where the medium contacts a membrane. The membrane device 200, 300 allows for passage of spent medium with cellular products through the large pore membrane while retaining dissolvable microcarriers in the vessel 110. Simultaneously, or subsequent to removing 506 spent medium from the vessel 110, the perfusion cell culture method 500 as described herein may further include adding 508 fresh medium to the vessel 110. The volume of fresh medium added to the vessel 110 may be approximately equal to the volume of spent media removed through the large pore membrane device 200.

The rate at which spent medium is replaced with fresh medium, or the rate of perfusion, may be any rate appropriate to efficient growth of cells. For example, the rate of perfusion may be between about 0.1 vessel volume exchanges per day (vvd) and about 20 vvd, or between about 0.5 vvd and about 10 vvd, or even between about 0.5 vvd and about 2.5 vvd. The rate of perfusion can remain constant over a period of time, or can be altered (i.e., increased or decreased) over the course of a period of perfusion, or any combination thereof. Further, an increase or decrease in the rate of perfusion can be applied in any manner known in the art, including, but not limited to, a steady alteration over time, e.g., a steady increase during a period of perfusion, or a series of alterations over time, e.g., a series of steady alterations, a series of stepwise alterations (e.g., the rate of perfusion could be increased or decreased in a stepwise manner), or any combination thereof. The timing of the initiation and cessation of a perfusion period, and of any alterations to the perfusion, can be predetermined, e.g., at a set time or interval, or based upon the monitoring of some parameter of the conditions in the bioreactor system 100. The perfusion can be applied in a continuous manner or in an intermittent manner. As used herein, continuous perfusion is performed continuously for 24 hours per day. Alternatively, intermittent perfusion is performed for only a fraction of a day (for example, four, six, eight, or ten hours of perfusion per day). In intermittent perfusion, higher rates of addition/removal of medium may be used to perform nearly the same degree of addition of fresh medium and removal of spent medium with cellular products.

According to embodiments of the present disclosure, the perfusion cell culture method 500 as described herein may further include dissolving 510 the dissolvable microcarriers. Dissolving 510 the dissolvable microcarriers includes exposing the microcarriers to a condition which causes the dissolvable microcarrier to enter solution. Dissolving 510 the dissolvable microcarriers releases cells from the surface of the dissolvable microcarriers into the medium of the vessel 110. As one example, dissolving 510 the dissolvable microcarriers may include adding 510 a digestion agent to the vessel 110. The digestion agent may include enzymes as described above in concentrations of between about 1 and about 200 U. For example, the digestion agent may include between about 2 U and about 150 U, or between about 5 U and about 100 U, or even between about 10 U and about 75 U, and all values therebetween. The digestion agent may also include a chelating agent. The digestion agent may include chelating agents as described above in concentrations of between about 1 mM and about 200 mM. For example, the digestion agent may include chelating agent concentrations of between about 10 mM and about 150 mM, or between about 20 mM and about 100 mM, or even between about 25 mM and about 50 mM, and all values therebetween.

The time for the dissolvable microcarriers to be completely dissolved as described herein may be less than about 1 hour. For example, the time for the dissolvable microcarriers to be completely dissolved may be less than about 45 minutes, or less than about 30 minutes, or less than about 15 minutes, or between about 1 minute and about 25 minutes, or between about 3 minutes and about 20 minutes, or even between about 5 minutes and about 15 minutes. As used herein, the term "completely dissolved" refers to the microcarrier material being in solution in at least one of monomeric form, dimeric form or oligomeric form.

Following dissolving 510 the dissolvable microcarriers, the perfusion cell culture method 500 as described herein may further include removing 512 spent medium and buffer with dissolved microcarrier material from the vessel 110 by flowing medium from the vessel 110 of the bioreactor system 100 to a small pore membrane device 300. Optionally, removing 512 spent medium with dissolved microcarrier material from the vessel 110 may include pumping the medium from the vessel 110 to an external recirculation loop that is fluidly connected to the vessel 110 where the medium contacts a small pore membrane. The small pore membrane device 300 allows for passage of spent medium with cellular waste products through the small pore membrane while retaining cells in the vessel 110. In addition to cellular waste products, the remaining digestion agent and the dissolved microcarrier material may also pass through the small pore membrane and be removed from the vessel 110. Simultaneously, or subsequent to removing 512 spent medium and buffer with dissolved microcarrier material from the vessel 110, the perfusion cell culture method 500 as described herein may further include adding 514 fresh medium to the vessel 110. The volume of fresh medium added to the vessel 110 may be approximately equal to the volume of spent media removed through the small pore membrane device 300.

As shown in FIG. 3, the perfusion cell culture method 500 as described herein may optionally include repeating adding 504 dissolvable microcarriers (with or without medium) to the vessel 110 of a bioreactor system 100. In particular, after dissolving 510 the dissolvable microcarriers, additional microcarriers may be added to the vessel 110 and further growth and proliferation of the cells may proceed on the surfaces of the subsequently added dissolvable microcarriers. As another option, the perfusion cell culture method 500 as described herein may include repeating adding 504 dissolvable microcarriers (with or without additional medium) to the vessel 110 of a bioreactor system 100 prior to dissolving 510 the dissolvable microcarriers. When performing the method in such a manner, microcarrier-to-microcarrier transfer of cells from initially added dissolvable microcarriers to subsequently added microcarriers may be leveraged. Leveraging microcarrier-to-microcarrier transfer beneficially provides a greater amount of surface area on which cells may grow. Where adding 504 dissolvable microcarriers is repeated and includes adding medium, the total the medium volume within the vessel 110 may be increased. Such increase in volume may allow for a greater number of dissolvable microcarriers to be in the vessel 110 and may provide a larger volume of medium and more surface area for cell growth.

Following removing 512 spent medium with dissolved microcarrier material from the vessel 110, the perfusion cell culture method 500 as described herein may further include forming 516 a solution containing the cells or cell products within the vessel 110. Once the solution is formed, the method may further include removing 518 the solution containing the cells or cell products from the vessel 110. Forming 516 a solution may include adding a buffer selected based on the intended use of the cells or cell products following removal from the vessel 110. For example, the buffer may be a harvest buffer which maintains an environment (for example, pH conditions) for the cells or cell products to remain viable for downstream processing steps, including filtration, capture, and chromatography operations. As another example, the buffer may be a formulation buffer, or a composition which allows for the cells or cell products to be used in therapeutic applications after being removed from the vessel 110. Forming 516 a solution may also include adding a cryprotectant, or a composition used to protect the cells or cell products from freezing damage, to the vessel 110 such that the cells can be cryopreserved after being removed from the vessel 110. Advantageously, embodiments of the present disclosure allow for removing 512 spent medium with dissolved microcarrier material from the vessel 110 without adding additional medium to the vessel 110. Instead, substantially all of the spent medium may be removed and then the cells or cell products within the vessel 110 may be re-concentrated in the solution without having to collect the cells or cell products to be re-suspended in a separate system or vessel.

According to an aspect (1) of the present disclosure, a perfusion bioreactor system is provided. The system comprises: a vessel having a wall at least partially defining an interior compartment for receiving fluid; at least one port fluidly connected to at least one of a plurality of external sources; and at least one outlet fluidly connected to a small pore membrane device.

According to an aspect (2) of the present disclosure, the system of aspect (1) is provided, wherein the small pore membrane device comprises an external recirculation loop fluidly connected to the at least one outlet.

According to an aspect (3) of the present disclosure, the system of any of aspects (1)-(2) is provided, wherein the small pore membrane device comprises a membrane having an average pore size that prevents the passage of cells through the membrane.

According to an aspect (4) of the present disclosure, the system of any of aspects (1)-(3) is provided, wherein the small pore membrane device comprises a membrane having an average pore size of between about 0.01 μm and about 1.0 μm.

According to an aspect (5) of the present disclosure, the system of any of aspects (1)-(4) is provided, further comprising a large pore membrane device fluidly connected to the at least one outlet.

According to an aspect (6) of the present disclosure, the system of aspect (5) is provided, wherein the large pore membrane device comprises an external recirculation loop fluidly connected to the at least one outlet.

According to an aspect (7) of the present disclosure, the system of any of aspects (5)-(6) is provided, wherein the large pore membrane device comprises a membrane having an average pore size that prevents the passage of dissolvable microcarriers through the membrane.

According to an aspect (8) of the present disclosure, the system of any of aspects (5)-(7) is provided, wherein the large pore membrane device comprises a membrane having an average pore size of between about 1 μm and about 100 μm.

According to an aspect (9) of the present disclosure, the system of any of aspects (1)-(8) is provided comprising a plurality of ports, each port being fluidly connected to one of the plurality of external sources.

According to an aspect (10) of the present disclosure, the system of any of aspects (1)-(8) is provided comprising one port fluidly connected to a common tubing manifold, the common tubing manifold being fluidly connected to the plurality of external sources.

According to an aspect (11) of the present disclosure, the system of any of aspects (1)-(8) is provided further comprising an aseptic connector in fluid communication with the at least one port.

According to an aspect (12) of the present disclosure, the system of any of aspects (1)-(11) is provided comprising a plurality of outlets.

According to an aspect (13) of the present disclosure, the system of any of aspects (1)-(12) is provided, wherein the vessel is a flexible vessel comprising a plastic film or a plastic laminate.

According to an aspect (14) of the present disclosure, the system of aspect (13) is provided, wherein the flexible vessels comprises at least one plastic material selected from the group consisting of polyethylene (PE), polypropylene (PP), polyvinyl chloride (PVC), polyethylene terephtalate (PET), polystyrene (PS), polycarbonate (PC), polymethylpentene (PMP), polyetheretherketone (PEEK) polytetrafluoroethylene (PTFE), polyfluoroalkoxy (PFA), polychlorotrifluoroethylene (PCTFE), ethylene vinyl acetate (EVA), and derivatives thereof.

According to an aspect (15) of the present disclosure, the system of any of aspects (1)-(12) is provided, wherein the vessel is a rigid vessel.

According to an aspect (16) of the present disclosure, the system of aspect (15) is provided, wherein the rigid vessels comprises at least one plastic material selected from the group consisting of high density polypropylene (HDPE), ultrahigh molecular weight (UHMW) polyethylene, polypropylene, EVA, LDPE and LLDPE.

According to an aspect (17) of the present disclosure, the system of aspect (15) is provided, wherein the rigid vessels comprises glass.

According to an aspect (18) of the present disclosure, a perfusion cell culture method is provided. The method comprises: adding cells and cell growth medium to a vessel of a bioreactor system; adding dissolvable microcarriers to the vessel; removing spent medium by flowing medium from the vessel to at least one membrane device fluidly connected to the vessel; adding fresh medium to the vessel to replace the removed spent medium; dissolving the dissolvable microcarriers; and removing spent medium with dissolved microcarrier material from the vessel by flowing medium from the vessel to the at least one membrane device fluidly connected to the vessel.

According to an aspect (19) of the present disclosure, the method of aspect (18) is provided, wherein removing spent medium comprises flowing medium from the vessel to a large pore membrane device fluidly connected to the vessel.

According to an aspect (20) of the present disclosure, the method of any of aspects (18)-(19) is provided, wherein removing spent medium with dissolved microcarrier material comprises flowing medium from the vessel to a small pore membrane device fluidly connected to the vessel.

According to an aspect (21) of the present disclosure, the method of any of aspects (18)-(20) is provided further comprising forming a solution containing cells or cell products within the vessel.

According to an aspect (22) of the present disclosure, the method of aspect (21) is provided, wherein forming a solution comprises adding a harvest buffer to the vessel.

According to an aspect (23) of the present disclosure, the method of aspect (21) is provided, wherein forming a solution the buffer comprises adding a formulation buffer to the vessel.

According to an aspect (24) of the present disclosure, the method of aspect (21) is provided, wherein forming a solution the buffer comprises adding a cryprotectant to the vessel.

According to an aspect (25) of the present disclosure, the method of any of aspects (21)-(24) is provided further comprising removing the solution containing cells or cell products from the vessel.

According to an aspect (26) of the present disclosure, the method of any of aspects (18)-(25) is provided comprising removing spent medium and adding fresh medium to the vessel to replace the removed spent medium at least twice prior to dissolving the dissolvable microcarriers.

According to an aspect (27) of the present disclosure, the method of any of aspects (18)-(26) is provided further comprising adding fresh medium to the vessel to replace the removed spent medium with dissolved microcarrier material.

According to an aspect (28) of the present disclosure, the method of any of aspects (18)-(27) is provided, wherein dissolving the dissolvable microcarriers comprises adding a digestion agent to the vessel.

According to an aspect (29) of the present disclosure, the method of aspect (28) is provided, wherein the digestion agent comprises non-proteolytic enzymes.

According to an aspect (30) of the present disclosure, the method of any of aspects (28)-(29) is provided, wherein the digestion agent comprises a non-proteolytic enzyme concentration of between about 1 U and about 200 U.

According to an aspect (31) of the present disclosure, the method of any of aspects (28)-(30) is provided, wherein the digestion agent comprises a chelating agent.

According to an aspect (32) of the present disclosure, the method of aspect (31) is provided, wherein the digestion agent comprises a chelating agent concentration of between about 1 mM and about 200 mM.

According to an aspect (33) of the present disclosure, the method of any of aspects (18)-(32) is provided, wherein dissolving the dissolvable microcarriers comprises completely dissolving the dissolvable microcarriers in less than about 1 hour.

According to an aspect (34) of the present disclosure, the method of any of aspects (18)-(33) is provided, wherein dissolving the dissolvable microcarriers comprises completely dissolving the dissolvable microcarriers in less than about 15 minutes.

According to an aspect (35) of the present disclosure, the method of any of aspects (18)-(34) is provided, wherein dissolving the dissolvable microcarriers comprises completely dissolving the dissolvable microcarriers in between about 1 minute and about 25 minutes.

According to an aspect (36) of the present disclosure, the method of any of aspects (18)-(35) is provided, further comprising, subsequent to removing spent medium with dissolved microcarrier material, adding dissolvable microcarriers to the vessel.

According to an aspect (37) of the present disclosure, the method of any of aspects (18)-(36) is provided, further comprising, prior to dissolving the dissolvable microcarriers, adding additional dissolvable microcarriers to the vessel.

According to an aspect (38) of the present disclosure, the method of any of aspects (18)-(37) is provided comprising between about 0.1 and about 20 vessel volume exchanges per day.

According to an aspect (39) of the present disclosure, the method of any of aspects (18)-(38) is provided comprising between about 0.5 and about 10 vessel volume exchanges per day.

According to an aspect (40) of the present disclosure, the method of any of aspects (18)-(39) is provided comprising between about 0.5 and about 2.5 vessel volume exchanges per day.

While the present disclosure includes a limited number of embodiments, those skilled in the art, having benefit of this disclosure, will appreciate that other embodiments can be devised which do not depart from the scope of the present disclosure.

What is claimed:

1. A perfusion bioreactor system comprising:
   a vessel having a wall at least partially defining an interior compartment for receiving fluid;
   at least one port fluidly connected to at least one of a plurality of external sources;
   a small pore membrane device comprising a first external recirculation loop that is fluidly connected to a first outlet from the vessel and a first inlet to the vessel; and
   a large pore membrane device comprising a second external recirculation loop that is fluidly connected to a second outlet from the vessel and a second inlet to the vessel;
   wherein the small pore membrane device comprises a membrane having an average pore size of between 0.01 lam and 1.0 µm, and
   wherein the large pore membrane device comprises a membrane having an average pore size of between 1 µm and 100 µm.

2. The perfusion bioreactor system of claim 1, wherein the small pore membrane device comprises a membrane having an average pore size that prevents the passage of cells through the membrane.

3. The perfusion bioreactor system of claim 1,
   wherein the large pore membrane device comprises a membrane having an average pore size that prevents the passage of dissolvable microcarriers through the membrane.

4. The perfusion bioreactor system of claim 1, further comprising a plurality of ports, each port being fluidly connected to one of the plurality of external sources.

5. The perfusion bioreactor system of comprising one port fluidly connected to a common tubing manifold, the common tubing manifold being fluidly connected to the plurality of external sources.

6. The perfusion bioreactor system of claim 1, further comprising an aseptic connector in fluid communication with the at least one port.

7. The perfusion bioreactor system of claim 1, further comprising a plurality of outlets.

* * * * *